United States Patent [19]

Sagner

[11] Patent Number: 5,243,409
[45] Date of Patent: Sep. 7, 1993

[54] APPARATUS FOR MEASURING OPTICAL DENSITY IN SITU

[75] Inventor: Max Sagner, Paris, France

[73] Assignee: Societe Nationale Elf Aquitaine, Courbevoie, France

[21] Appl. No.: 730,944

[22] PCT Filed: Jan. 30, 1990

[86] PCT No.: PCT/FR90/00072
§ 371 Date: Aug. 28, 1991
§ 102(e) Date: Aug. 28, 1991

[87] PCT Pub. No.: WO90/08818
PCT Pub. Date: Aug. 9, 1990

[30] Foreign Application Priority Data

Jan. 31, 1989 [FR] France ............... 89 01165

[51] Int. Cl.$^5$ ............... G01N 21/53; G01N 21/85; C12M 1/34
[52] U.S. Cl. ............... 356/436; 356/440; 356/442
[58] Field of Search ............ 356/434, 436, 440, 441, 356/442; 250/576; 73/863.73, 864.83, 864.84

[56] References Cited

U.S. PATENT DOCUMENTS

| 2,866,379 | 12/1958 | Veit | 356/441 |
|---|---|---|---|
| 3,164,663 | 1/1965 | Gale | 356/436 |
| 3,814,930 | 6/1974 | Lindberg | 356/442 |
| 3,876,307 | 4/1975 | Skala | 356/434 |
| 3,962,041 | 6/1976 | Müller et al. | 356/441 |
| 4,085,618 | 4/1978 | Collins | 73/863.73 |
| 4,135,100 | 1/1979 | Harada et al. | 356/440 |
| 4,188,126 | 2/1980 | Boisde et al. | 356/440 |
| 4,451,152 | 5/1984 | Topol et al. | 356/440 |
| 4,725,148 | 2/1988 | Endo et al. | 356/442 |
| 4,943,735 | 7/1990 | Nishikawa | 250/573 |
| 5,046,854 | 9/1991 | Weller et al. | 250/576 |

FOREIGN PATENT DOCUMENTS

| 1959612 | 6/1971 | Fed. Rep. of Germany | 356/432 |
|---|---|---|---|
| 2412038 | 10/1974 | Fed. Rep. of Germany | . |
| 2534763 | 3/1976 | Fed. Rep. of Germany | . |
| 38388 | 4/1978 | Japan | 356/434 |

OTHER PUBLICATIONS

Patent Abstracts of Japan, vol. 10, No. 229, abstract No. 61-65123 (Aug. 8, 1986).
Patent Abstracts of Japan, vol. 12, No. 288, abstract No. 63-65345 (Aug. 8, 1988).
Patent Abstracts of Japan, vol. 9, No. 167, abstract No. 60-44851 (Jul. 12, 1985).

Primary Examiner—Richard A. Rosenberger

[57] ABSTRACT

A device for measuring in situ, the optical density of a sample in a medium, in which the immersed sample has a main part with a slot at one end. A mobile part can be lodged in this slot. This mobile part has an open chamber which moves with the mobile part into the slot. This open chamber will contain a sample and will be aligned with an optical device in the housing, when moved into the slot. The mobile part and open chamber are, therefore, movable between an open position in which the medium to be studied circulates in the chamber, to a closed position when the mobile part is lodged in the slot whereat the open chamber is isolated from the medium to be studied. Measurement is carried out while the device is in the closed position by measuring the optical density of the isolated medium.

13 Claims, 3 Drawing Sheets

APPARATUS FOR MEASURING OPTICAL DENSITY IN SITU

FIELD OF THE INVENTION

The present invention relates to an apparatus for measuring the optical density in situ of a reaction medium, particularly in a fermenter.

DESCRIPTION OF BACKGROUND ART

Measurement of the biomass is very important for monitoring and operating bioreactors, both in process development laboratories and in production facilities.

Usually this measurement is performed either by removing a sample of the reaction medium then counting the number of cells under the microscope in the laboratory, which is a very long process, i.e., more than 12 hours, or by calculating the optical density, which is the logarithm of the ratio between the "entering" intensity of a light flux upon its emission and the "exiting" intensity of this same flux after it has passed through a certain length of a sample of the reaction medium contained in the fermenter. For a given reaction, the optical density in transmission is a value that is well correlated with the quantity of biomass of the reaction medium, and the measurement thereof permits indirectly evaluating the bacterial concentration of the medium.

In a device for measuring optical density manufactured and sold by the Swiss company CHEMAP, the measurement is performed in a cell situated outside the fermenter. This measuring device is connected to the fermenter by a thin tube with a length of approximately several tens of centimeters, through which there is sucked the sample of reaction medium upon which the measurement is performed, the tube remaining permanently open to the fermenter. The operating principle of the cell is quite similar to that of a syringe, the measuring cell belonging to the reservoir of the syringe: a portion of the liquid contained in the fermenter is first sucked into the cell and, to avoid the situation that the bubbles contained in this liquid falsify the measurement of optical density, the liquid is allowed to rest for some tens of seconds, the time in which the bubbles migrate to the upper part of the cell. The measurement is then performed by comparing the intensity of the light flux at the entrance of the cell with the intensity of this flux at the exit of the cell, then, once the measurement has been performed, the liquid is reinjected into the fermenter. To take into account possible variations of the intensity of the light source emitting the light flux, the optical density through the liquid sample and the light intensity emitted by the source are measured simultaneously. Thus the result can be calibrated. In addition, a system of small wipers permits, in this device, cleaning by scraping the optical surfaces between two measurements.

A first drawback of this apparatus is its bulkiness; a second drawback is that there exists a risk of defective sterilization and, because the tube is open to the medium, of pollution of the fermentation process. Routine use of this apparatus can pose problems in production.

In U.S. Pat. No. 4,725,148, there is described a device that permits measurement in situ, therefore without sampling steps, of the optical density of the reaction medium contained in a fermenter. The device in this case is inside a mechanical system sunk into the shell of the fermenter, such that its lower part dips into the reaction medium.

In the lower part of the apparatus there is provided, by way of a cell, a space that is open to the reaction medium such that this circulates freely therein. The measurement of biomass in this case is also performed by comparison of the intensity of an emitted light flux and the intensity of this same flux received after passage through a known thickness of the reaction medium to be studied. The light source of this device is a semiconductor laser diode providing a constant intensity, such that calibration is not necessary, and the receiver is a semiconductor diode. A cooling loop limits the temperature of the device, such that the apparatus can remain in place during the sterilization phases. To avoid the situation that the bubbles disturb the measurement, a screen is placed at the entrance of the cell. This screen must not be too fine, in order that it not prevent the large particles contained in the reaction medium from entering the cell: the measurement performed would then not be representative of the real state of the medium, especially at the end of fermentation. The small bubbles of diameter smaller than the spacing of the screen will therefore be able to perturb the measurement: if, for example, the rate of agitation of the medium is changed, the number and the size of the bubbles vary and the measurement risks being different. Another problem is that this screen becomes fouled quite rapidly and that it is not provided with means for cleaning it.

SUMMARY OF THE INVENTION

The device for measuring optical density according to the invention, while retaining the advantages of the prior art, permits overcoming certain of its drawbacks.

The principle used consists of enclosing a sample of the reaction medium in an in situ measuring cell, waiting after closure of the cell for the bubbles to collect in the upper part of the cell, then performing the measurement of optical density, by transmission, in the lower part thereof.

The device according to the invention consists for this purpose of a main part forming the body of the device in which there is provided a housing, of a movable part which can be housed in the housing of the main part and in which there is provided a cavity that is open to the outside of the movable part via at least two opposite orifices capable of being joined up, of optical means included in the main part on both sides of the housing, to conduct a light flux from a source to a light analyzer, of means for shifting the movable part from an open position in which the medium to be studied circulates freely in the cavity of the movable part to a closed position in which the movable part is sunk into the housing of the main part, such that the cavity and its contents, constituting the sample of the medium to be analyzed, on which sample the measurement will be performed, are isolated from the medium to be studied, the optical means being adapted as a function of the position of the orifices of the movable part such that the light flux passes through the contents of the cavity when the movable part is in closed position. Means for calibrating the measurements and means for cleaning the optical surfaces for each measurement are also provided.

The calibration means consist of at least one reference optical bar, which consists of glass or of quartz, for example, of known characteristics, particularly the transmission coefficient, and which will be placed, at least momentarily, in the optical path of the light flux. In the case in which there is more than one calibration bar, these will preferentially be of different transmission coefficients, which permits calibration over a plurality of points and a scan of greater dynamic range than with a single bar, and this without disassembly. The calibration bars will preferentially be placed in the thickness of the movable part.

The cleaning means can consist of brush scrapers, for example, placed on the movable part to clean the optical surfaces of the main part, and of scrapers or brushes situated on the main part to clean the optical surfaces of the movable part. The cleaning means remove in particular the small bubbles that could remain attached to the optical surfaces.

The elements of the device according to the invention are resistant to temperatures of several hundred degrees, and so sterilization while leaving the device in place is possible.

In one preferential embodiment, sampling is performed by rotation of the movable part around a motor-controlled axis of rotation.

The optical means can consist of a single bundle of bifurcated optical fibers connecting the housing on the one hand to the source and to the analyzer on the other hand, and of a reflector situated at the surface of the housing, facing the end of the optical fiber bundle opening onto the housing, the end of the fiber bundle and the reflector being placed in such a fashion that each is facing one orifice of the cavity of the movable part when this is in closed position, the two orifices being in opposite relationship.

According to another embodiment, the fiber bundle consists of simple fibers all having their end opening onto the housing of the main part, half of them, the "outgoing" fibers, connecting the housing to the source, and the other half, the "return" fibers, connecting the housing to the light analyzer, the "outgoing" fibers and the "return" fibers being distributed randomly in the bundle.

Preferentially, the movable part is a disk with parallel bases, inscribed in a circle, the thickness of which disk is equal to the width of a recess made in the end of the main part, the recess being perpendicular to the axis of the main part and constituting the housing.

The cavity can have rotational symmetry around an axis perpendicular to the two disk bases constituting the movable part, and is open toward the outside via two orifices of circular section: the cavity can be, among other possibilities, a cylinder, a cone or a double cylinder of T-shaped cross section.

The cavity provided in the movable part can also be a sector open to the outside via the upper base, the lower base and the lateral face of the movable part, the two orifices of the cavity of the movable part being joined up, and the bases of the movable part assuming a V-shaped or U-shaped form.

The device is of very small dimension, on the order of 80 mm in length and 25 mm in diameter. It can be placed either in one of the connection pieces that are normally provided in the base of fermenters and that are intended to receive one or more measuring apparatuses, i.e., such as the device described in U.S. Pat. No. 4,725,148, inside a mechanical system sunk into the shell of the fermenter. Thus the device which, for example, can be mounted on a leaktight cover that screws onto the connection piece or onto the mechanical system, can easily be removed for cleaning, among other operations. Once put in place, the device dips into the reaction mixture contained in the fermenter, especially its lower base in which the movable part is located.

The device according to the invention therefore permits monitoring, in situ and in real time, the fermentation process in particular, while becoming free of problems of pollution of the measurement resulting from the presence of microscopic bubbles and of fermentation residues, from interference by the ambient light, which in the open systems creates measurement noise that must be eliminated by modulation, an operation that is not necessary here, or from variation of light intensity. By virtue of its small size and the ease of cleaning and sterilizing it, this device does not pose problems in production.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Other characteristics and advantages of the present invention will appear more clearly upon reading the description hereinafter, written with reference to the attached figures which are given by way of illustration only, and thus are not limitative of the present invention, and wherein.

DETAILED DESCRIPTION OF THE PREFERRED EMBODIMENT

Figure 1:
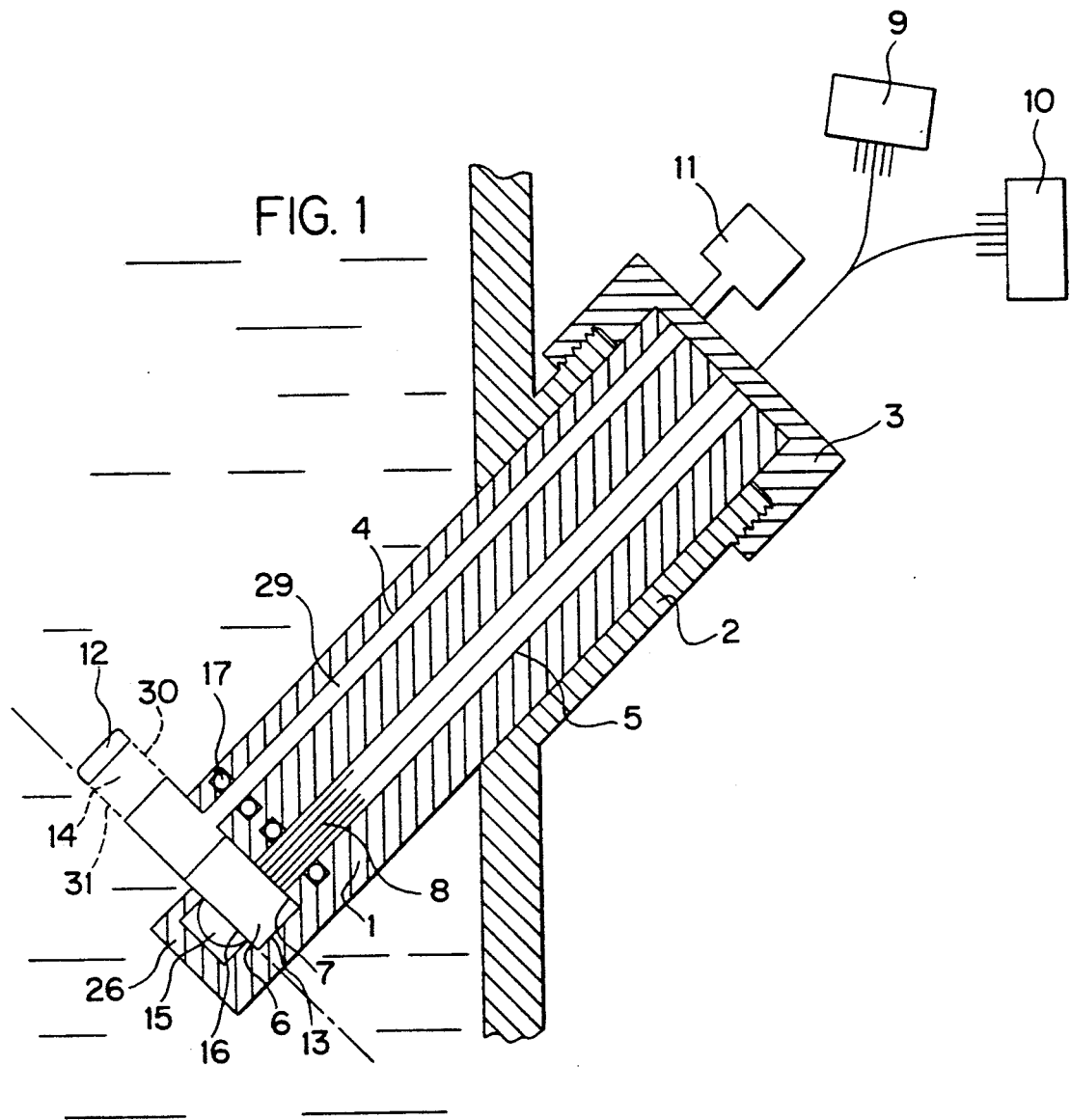
FIG. 1 is a longitudinal section of the device according to a preferred embodiment, making it possible to understand how the device is placed through the shell of the tank containing the medium to be studied.
Figure 2A:
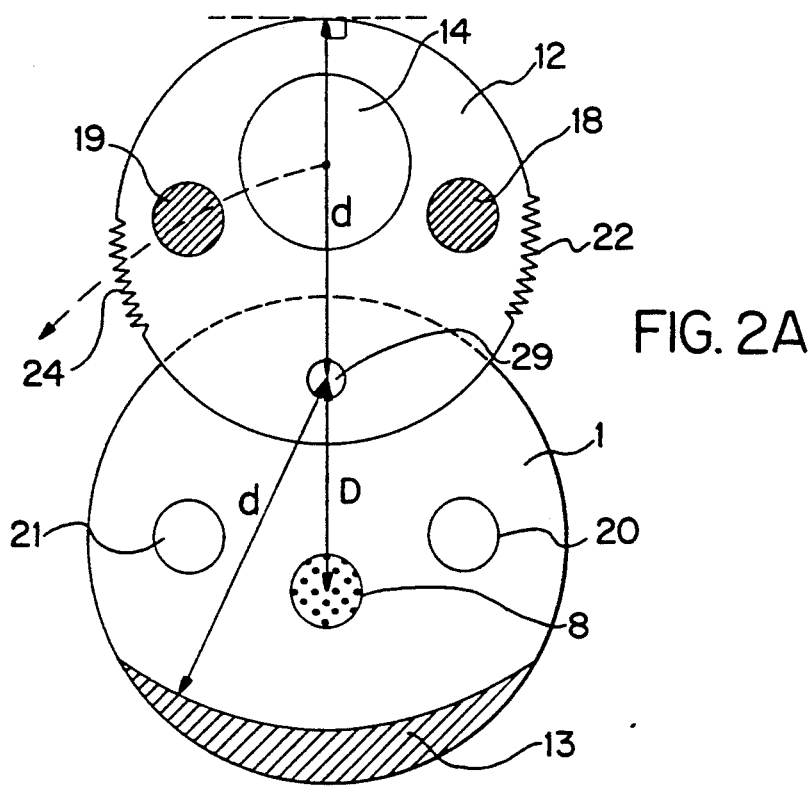
FIGS. 2A and 2B represent two transverse sections at the location of the movable part, for two possible embodiments of the movable piece driven by a rotational movement, one with circular base and cylindrical cavity (FIG. 2A), the other with triangular base and cavity of sector form (FIG. 2B)

A device according to the invention, as it can appear once put in place, is represented in longitudinal section in FIG. 1 and in transverse section in FIG. 2A. The device contains a main part 1, especially of stainless metal, which is a cylinder of about 80 mm length, the circular section of which has a diameter of 25 mm, for example. This part 1 is maintained in a connection piece 2 of the shell of the fermenter tank by a cover 3, with which the part 1 is integral and which is screwed onto the connection piece 2. Along any desired diameter of the cross section of the main part, such diameter defining the section plane of FIG. 1, there are drilled two holes 4 and 5 of the same length in the main part, on both sides of the center of the diameter, at any desired distances apart.

Figure 3A:
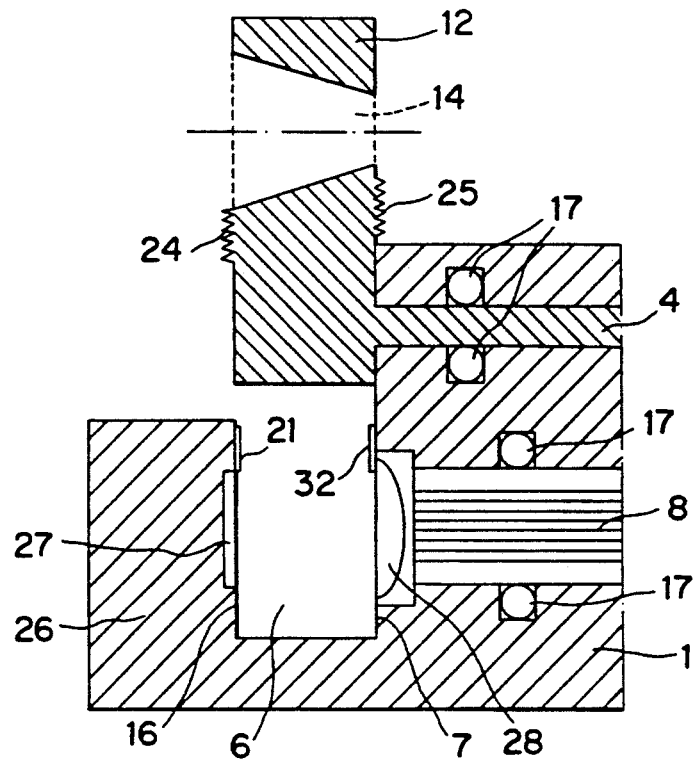
FIGS. 3A and 3B represent two longitudinal sections of the end of the device at the location of the movable part for two other possible embodiments of the said movable part and of the cavity.
Figure 3B:
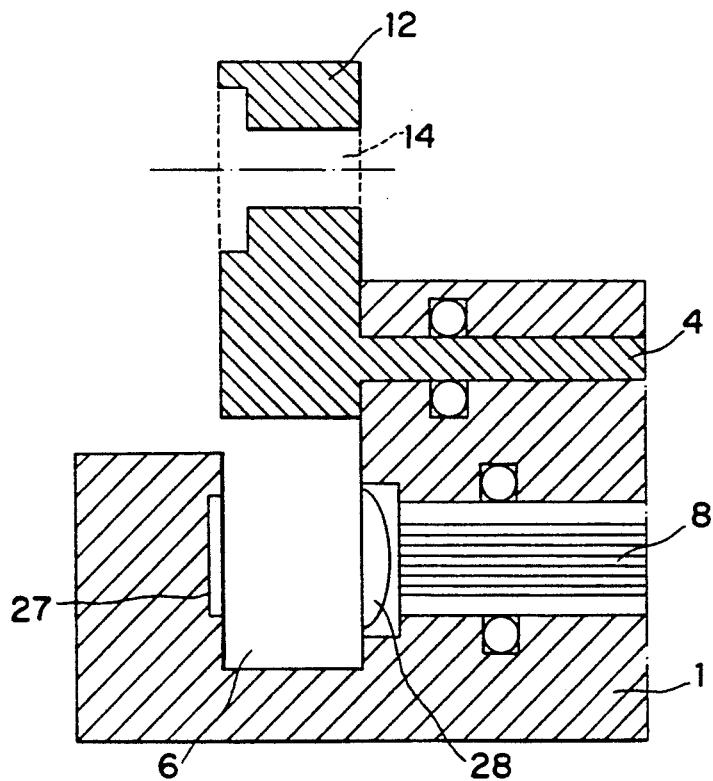

The holes, which have the same direction as the axis of the part 1, pass through the main part over almost its entire length, the undrilled portion opposite the end attached to the cover 3 being defined as the lower portion of the part. At about ten millimeters from the lower end of the main part, a deep recess 6 is made along a plane perpendicular to the axis of the main part. This recess has for axis of symmetry an axis parallel to the diameter passing through the holes 4 and 5, and has a width of between 5 and 15 mm. It constitutes the housing of the main part in which the movable part will be housed. The recess is bounded by two parallel walls, the upper wall 7 and the lower wall 16. The recess separates the upper portion of the main part, which is closest to the shell of the tank, from its lower portion 26. The surface areas of the two walls 7 and 16 are in principle equal, although the surface area of the wall 16 may be reduced by the fact of elimination of the non-useful volume of the lower portion 26, in order to economize on material, as is shown in FIGS. 1, 3A and 3B.

Figure 2B:
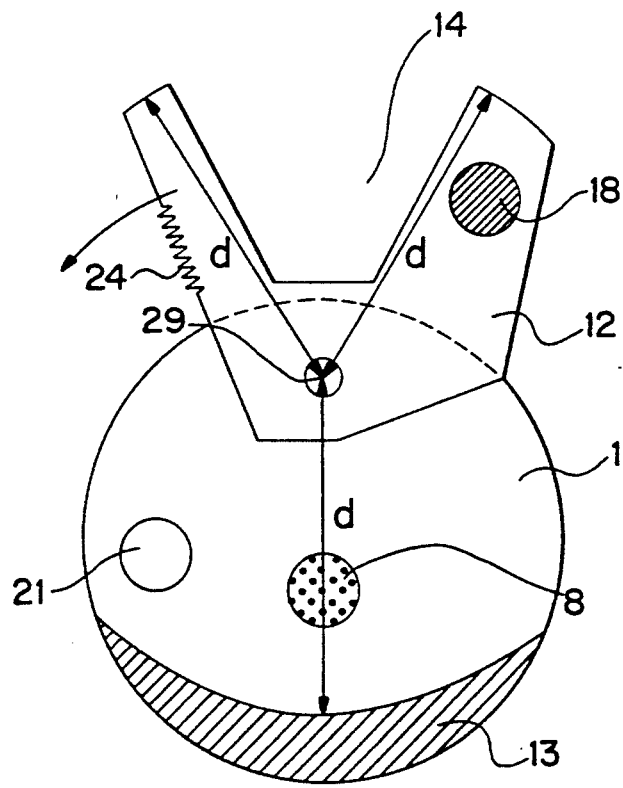

The bottom of the recess is machined in the form of an arc of a circle, the center of which is situated on the lower end of the axis of rotation (or a rotation rod) 29, at its attachment to the movable part, and the radius of which is larger than that of the cross section of the main part. This radius is such that the thickness of the bottom 13 is such that this bottom offers sufficient resistance, which is a function, among other factors, of the force exerted on the lower portion of the main part. The bottom 13 connecting the upper portion of the main part to its lower portion, one face of which bottom is constituted by the bottom of the recess, has a section in the form of a crescent moon, as shown in FIGS. 2A and 2B.

Each of the holes 4 and 5 opens onto the upper wall 7 of the recess. The hole 5, which is that which opens closer to the bottom of the recess, contains a bundle 8 of optical fibers. At the opening onto the recess, the fibers are grouped, bonded and polished, their surface coinciding exactly with the wall of the recess. At the upper end of the hole 5, half of the fibers are connected, through the cover 3, to a light source 9, the second half of the fibers being connected, through the cover 3, to a photometer 10, the fibers connected to the source or to the analyzer being distributed randomly in the bundle 8.

As shown in FIG. 1, the bundle of simple fibers can be replaced by a bundle of bifurcated fibers having three branches connected at one coupling point. One is assigned to the outgoing and return travel of the light flux and is situated in the hole 5, the second connects the coupling point to the light source 9, and the third connects the coupling point to the photometer 10. The coupling of the branches is effected at the location of the cover 3 or outside the connection piece. The source and photometer are outside the tank.

The fibers can be made of quartz, which is resistant to temperatures of several hundred degrees.

In the second hole 4 there is housed an axis of rotation 29, connected through the fixing cover 3 to a control motor 11 outside the tank and at its other end to an off-center point of a cylindrical movable part 12, particularly of stainless metal, abutting against the upper wall 7 of the recess. This movable part is a disk, the thickness of which is equal to the width of the recess 6.

The diameter of the movable part is larger than the distance D that is present between the axis of rotation and the optical bundle, and is smaller than the diameter of the main part.

The distance d between the axis of rotation 29 and the furthest removed point of the disk 12 will be equal to or smaller than the radius of the circle corresponding to which the bottom of the recess is machined, such that the movable part can perform a rotation of 180° around the axis of rotation. For the practical examples described here, the dimensions of the parts are calculated such that the lateral face of the movable part and the bottom of the recess are contiguous for one position of the disk, called "closed", which is obtained after rotation of 180° relative to the position called "open", shown in FIGS. 2A or 2B.

The movable part is drilled through its entire thickness by a cylindrical hole 14 of diameter greater than that of the bundle of optical fibers, in such a manner as to define a cavity open to the outside of the movable part via two circular orifices 30 and 31 of identical surface area, each situated on one of the faces of the disk and in opposite relationship. Thus the fluid in which there dips the lower portion of the apparatus, including the movable part, can circulate freely in the cavity, for certain positions of the disk, called open positions.

The distance between the center of this cavity and the axis of rotation is equal to the distance D that is present between the axis of rotation and the bundle of optical fibers, such that there exists a particular position, in the course of rotation of the disk around the axis of rotation, called the closed position, for which the cylinder 14 is exactly in the extension of the bundle of optical fibers.

A reflecting convex mirror 15 with flat outer surface is inlaid in the lower wall of the recess, exactly in the extension of the fiber bundle 8. Thus, in closed position of the device, the reflector, the cylindrical cavity and its orifices and the end of the bundle are aligned, and the light flux guided by the "outgoing" fibers of the bundle 8 is reflected at this mirror 15 after having passed through the cavity 14 provided in the movable part and containing a sample of the medium to be studied, and is sent back at the end of the bundle and reconducted via the "return" fibers to the light analyzer 10, in this case a photometer.

Leaktightness at the location of the axis of rotation and of the bundle of optical fibers is ensured by O-rings 17 placed around the axis of rotation 29 and the bundle 8, close to the upper wall 7 of the recess.

Let D be the distance between the axis of rotation and the center of the hole containing the bundle of optical fibers. At the distance D from the axis of rotation, two cylindrical glass bars 18 and 19, of length equal to the thickness of the movable part and of diameter substantially equal to the diameter of the bundle of optical fibers, are included in the movable part along axes perpendicular to the bases of the part.

Thus, in transverse section, as represented in FIG. 2A, the bars and the end of the optical bundle are situated on the same circle having radius D and having the axis of rotation as its center, such that, during the rotation of the movable part around the axis of rotation, each of the bars is located at one moment in the extension of the bundle of optical fibers, between the end of the bundle and the mirror 15. The bars are of quartz, treated in such a fashion that their transmission coefficients are different, in order to scan a greater dynamic range than with a single bar, and this without disassembly.

On this same circle having the axis of rotation as its center and having radius D there are placed, on each of the walls of the recess of the main part, two small hair brushes 20 and 21, 32 and 33. The brushes are intended to clean the surfaces of the optical bars during the rotation of the movable part.

Small wipers 22, 23, 24, 25, intended to clean the surfaces of the bundle of optical fibers and surface of the mirror, are fixed to the lateral wall of the movable part in pairs and back-to-back in such a fashion that the hairs extend slightly beyond the upper and lower bases of the movable part.

The wipers are placed around the circumference of the movable part such that they pass over the optical surfaces—the end of the optical bundle and the surface of the reflector—during the rotation of the movable part.

FIGS. 2B, 3A and 3B show other possible embodiments of the movable part driven by a rotational movement, in particular different forms that can be assumed by the cavity that will contain the liquid sample on which the measurement will be performed.

In FIG. 2B, for example, the movable part has roughly a U-shaped form with thick branches, the volume is open to the reaction mixture via the upper and lower bases of the part and also via the side. A single calibration bar is provided here. In this case, the device will advantageously be inclined or oriented in such a fashion that these bubbles collect in a corner, called the upper corner, of the sector, the measurement of density being performed in the lower portion thereof. In FIG. 3A, the volume 14 is a diverging cone with axis of symmetry having the same direction as the axis of the main part. In FIG. 3B, the volume has a T-shaped section. These latter two geometries have the advantage that, regardless of the position of the system, the bubbles are trapped in the upper portion of the dihedral angle or in the portion of greater diameter. Therefore it is no longer necessary to position the system specially during fixation on the fermenter.

In these two latter cases, the convex mirror of FIG. 1 advantageously can be replaced by a plane mirror 27, and a collimating lens 28 resistant to elevated temperatures on the order of 750° C. can be interposed between the end of the fiber bundle.

Of course, the present invention is not limited to the described embodiments. On the contrary, it extends to any variant included in the scope of the claims hereinafter.

In particular, it is possible to envision a device in which the displacement of the movable part would no longer be a rotation but the simple sliding of a part, for example of cubic shape, partly cut away, in a main part in which a housing intended to receive the cubic movable part would be provided.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for measuring the optical density in situ of a medium comprising:
   a main part forming the body of the device, a housing being provided in the main part, the housing being located in the medium;
   a movable part which can be housed in said housing and in which an open cavity is provided, the cavity being open to the outside of the movable part via at least two opposite orifices;
   optical means in the main part on both sides of the housing for conducting a light flux from a source to a light analyzer through optical surfaces located on both sides of the housing; and
   means for shifting the movable part from an open position in which the medium to be studied circulates freely in the cavity of the movable part and the housing to a closed position in which the movable part is positioned within the housing of the main part, such that an interior of the housing, the cavity and contents thereof are isolated from the medium, the contents of the cavity constituting the sample of the medium to be analyzed, on which sample the measurement will be performed, the optical means being aligned with the orifices of the movable part when the movable part is in the closed position such that the light flux passes through the contents of the cavity and the contents of the cavity are isolated form the medium.

2. The device according to claim 1, further comprising means for calibrating intensity of the light flux and means for cleaning the optical surfaces.

3. The device according to claim 2, wherein the calibration means comprises at least one optical bar of known characteristics placed at least momentarily in the optical path of the light flux.

4. The device according to claim 3, wherein the calibration means comprises a plurality of calibration bars having different transmission coefficients.

5. The device according to claims 3 or 4, wherein the calibration bars are placed in the movable part and are movable therewith from a position in the optical path of the light flux to a position out of said optical path.

6. The device according to claim 2, wherein the cleaning means comprises at least one of scrapers and brushes place on the movable part to clean optical surfaces of the main part, and further comprising at least one of scrapers and brushes placed on the main part to clean optical surfaces of the movable part.

7. The device according to claim 1 or 2, wherein the device comprises elements that are resistant to sterilization temperature.

8. The device according to claim 1 or 2, wherein the means for shifting the movable part contains a rotation rod attached to the movable part and a motor for rotation of said rod.

9. The device according to claim 1 or 2, wherein the optical means comprises a bundle of bifurcated fibers connecting the housing to the source and the light analyzer, and the optical means comprises at least one reflector situated on the surface of the housing facing an end of the fiber bundle.

10. The device according to claim 1, wherein the movable part is a disk, the bases of which are inscribed in generally a circle and the thickness of which is equal to the width of a recess close to one end of the main part, the recess being generally perpendicular to the longitudinal axis of the main part and the recess constituting the housing.

11. The device according to claim 10, wherein the cavity of the movable part has an axis of symmetry generally perpendicular to the bases of the disk, which cavity is open to the outside via the two orifices which generally have circular sections.

12. The device according to claim 10, wherein the cavity provided in the movable part is a sector of the movable part.

13. The device according to claim 1, wherein the means for shifting is mounted off-center to the movable body and the means for shifting moves the movable body in an eccentric path.

* * * * *